(12) United States Patent
Opsal et al.

(10) Patent No.: US 6,671,047 B2
(45) Date of Patent: Dec. 30, 2003

(54) COMBINATION THERMAL WAVE AND OPTICAL SPECTROSCOPY MEASUREMENT SYSTEMS

(75) Inventors: Jon Opsal, Livermore, CA (US); Minna Hovinen, Fremont, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/346,389

(22) Filed: Jan. 17, 2003

(65) Prior Publication Data

US 2003/0137664 A1 Jul. 24, 2003

Related U.S. Application Data

(63) Continuation of application No. 09/499,974, filed on Feb. 8, 2000, now Pat. No. 6,535,285.

(51) Int. Cl.$^7$ .................................................. G01J 4/00

(52) U.S. Cl. ........................ 356/369; 356/364; 250/225

(58) Field of Search ............................... 356/369, 364, 356/365, 366, 367, 451, 453; 250/225

(56) References Cited

U.S. PATENT DOCUMENTS

| | | | |
|---|---|---|---|
| 4,634,290 A | 1/1987 | Rosencwaig et al. | 374/5 |
| 4,636,088 A | 1/1987 | Rosencwaig et al. | 347/5 |
| 4,854,710 A | 8/1989 | Opsal et al. | 356/432 |
| 4,999,014 A | 3/1991 | Gold et al. | 356/382 |
| 5,074,669 A | 12/1991 | Opsal | 356/445 |
| 5,181,080 A | 1/1993 | Fanton et al. | 356/381 |
| 5,206,710 A | 4/1993 | Geiler et al. | 356/432 |
| 5,536,936 A | 7/1996 | Drevillon et al. | 250/226 |
| 5,798,837 A | 8/1998 | Aspnes et al. | 356/369 |

(List continued on next page.)

FOREIGN PATENT DOCUMENTS

| | | | |
|---|---|---|---|
| WO | WO 99/10747 | 1/1999 | G01N/21/17 |
| WO | WO 00/68656 | 11/2000 | G01J/4/00 |

OTHER PUBLICATIONS

M. Fried et al., "Nondestructive determination of damage depth profiles in ion–implanted semiconductors by spectroscopic ellipsometry using different optical models," *J. Appl. Phys.*, vol. 71, No. 6, Mar. 15, 1992, pp. 2835–2843.

A.P. Webb et al., "Refractive index profiles induced by ion implantation into silica," *J. Phys. D: Appl. Phys.*, vol. 9, 1976, pp. 1343–1354.

J.R. Adams, "Complex refractive index and phosphorous concentration profiles in P31 ion implanted silicon by ellipsometry and auger electron spectroscopy," *Surface Science*, vol. 56, 1976, pp. 307–315.

J.R. Adams et al., "Determination of the complex refractive index profiles in P31 ion implanted silicon by ellipsometry," *Surface Science*, vol. 49, 1975, pp. 441–458.

J.P. Cortot et al., "Analysis of aresenic and phosphorus ion implanted silicon by spectroscopic ellipsometry," *Appl. Phys. Lett.*, vol. 41, No. 1, Jul. 1, 1982, pp. 93–95.

X–F. He et al., "Disorder effects on optical spectra and band structure of Si induced by ion implantation," *J. Appl. Phys.*, vol. 66, No. 11, Dec. 1, 1989, pp. 5261–5266.

(List continued on next page.)

*Primary Examiner*—Frank G. Font
*Assistant Examiner*—Roy M. Punnoose
(74) *Attorney, Agent, or Firm*—Stallman & Pollock LLP

(57) ABSTRACT

A combination metrology tool is disclosed which is capable of obtaining both thermal wave and optical spectroscopy measurements on a semiconductor wafer. In a preferred embodiment, the principal combination includes a thermal wave measurement and a spectroscopic ellipsometric measurement. These measurements are used to characterize ion implantation processes in semiconductors over a large dosage range.

8 Claims, 5 Drawing Sheets

U.S. PATENT DOCUMENTS

| | | | |
|---|---|---|---|
| 5,900,939 A | 5/1999 | Aspnes et al. | 356/243.1 |
| 5,953,446 A | 9/1999 | Opsal et al. | 382/141 |
| 5,973,787 A | 10/1999 | Aspnes et al. | 356/369 |
| 5,978,074 A | 11/1999 | Opsal et al. | 356/72 |
| 6,008,906 A | 12/1999 | Maris | 250/226 |
| 6,128,084 A | 10/2000 | Nanbu et al. | 356/369 |
| 6,191,846 B1 | 2/2001 | Opsal et al. | 356/364 |
| 6,268,916 B1 | 7/2001 | Lee et al. | 356/369 |
| 6,278,519 B1 | 8/2001 | Rosencwaig et al. | 250/225 |
| 6,535,285 B1 | 3/2003 | Opsal et al. | 356/369 |

OTHER PUBLICATIONS

T. Yamaguchi et al., "Empirical dielectric function of amorphous materials for spectroscopic ellipsometry," *J. Appl. Phys.*, vol. 77, No. 9, May 1, 1995, pp. 4673–4676.

Kravetsky, Kulyuk et al., "Reflected optical second harmonic generation as a method for caractereization of ion–implanted, thermal annealed silicon surfaces and silicon–insulator interfaces," *Ion Implanted Technology*, vol. 94, 1995, pp. 656–659.

D.E. Aspnes et al., "Dielectric properties of heavily doped crystalline and amorphous silicon from 1.5 to 6.0 eV," *Physical Review B*, vol. 29, No. 2, Jan. 15, 1984, pp. 768–779.

Y. Takeda et al., "Large third–order optical nonlinearity of tin microcrystallite–doped silica glass formed by ion implantation," *Appl. Phys. Lett.*, vol. 63, No. 25, Dec. 20, 1993, pp. 3420–3422.

J.M.C. England et al., "The dynamics of amorphous–to–crystalline interface evolution in ion–implanted polycrystalline silicon," *J. Appl. Phys.*, vol. 73, No. 9, May 1, 1993, pp. 4332–4343.

E. Chason et al., "In situ energy dispersive x≈ray reflectivity measurements of H ion bombardment on SiO2/Si and Si," *Appl. Phys. Lett.*, vol. 60, No. 19, May 11, 1992, pp. 2353–2355.

Y.Z. Hu et al., "A Comparison of Argon and Hydrogen Ion Etching and Damage in the Si–SiO2 System," *J. Electrochem. Soc.*, vol. 139, No. 7, Jul. 1992, pp. 2022–2026.

R.E. Hummel et al., "Ion Implantation Damage and Annealing of Silicon as Characterized by Differential Reflectometry," *J. Electrochem. Soc.*, vol. 137, No. 11, Nov. 1990, pp. 3583–3588.

N.V. Nguyen et al., "Spectroscopic ellipsometry studies of crystalline silicon implanted with carbon ions," *J. Appl. Phys.*, vol. 67, No. 8, Apr. 15, 1990, pp. 3555–3559.

G.F. Feng et al., "Optical properties of ion–implanted GaAs: The observation of finite–size effects in GaAs microcrystals," *Physical Review B*, vol. 40, No. 2, Jul. 15, 1989, pp. 1064–1073.

L. Chen et al., "Transient photomodulation spectroscopy of nanocrystalline hydrogenated silicon," *Physical Review B*, vol. 39, No. 8, Mar. 15, 1989, pp. 5121–5127.

A.H.M. Holtslag et al., "Noble–gas ion barbardment on clean silicon surfaces," *Physical Review B*, vol. 38, No. 15, Nov. 15, 1988, pp. 10556–10570.

R.E. Hummel et al., "Optical investigations of ion implant damage in silicon," *J. Appl. Phys.*, vol. 63, No. 8, Apr. 15, 1988, pp. 2591–2594.

J.L. Buckner et al., "Ellipsometric and Rutherford backscattering characterization of low–energy hydrogen–, helium–, neon–, and argon–bombarded silicon," *J. Appl. Phys.*, vol. 63, No. 11, Jun. 1, 1988, pp. 5288–5294.

J. Narayan et al., "Formation and nondestructive characterization of ion implanted silicon–on–insulator layers," *Appl. Phys. Lett.*, vol. 51, No. 5, Aug. 3, 1987, pp. 343–345.

P.J. McMarr et al., "Spectroscopic ellipsometry: A new tool for nondestructive depth profiling and characterization of interfaces," *J. Appl. Phys.*, vol. 59, No. 3, Feb. 1, 1986, pp. 694–701.

X.C. Mu et al., "Ar ion beam and CC14 reactive ion etching: A comparison of etching damage and of damage passivation by hydrogen," *J. Appl. Phys.*, vol. 58, No. 11, Dec. 1, 1985, pp. 4282–4291.

R.W. Collins et al., "A ellipsometry study of a hydrogenated amorphous silicon based n–i structure," *J. Appl. Phys.*, vol. 57, No. 10, May 15, 1985, pp. 4566–4571.

K. Vedam et al., "Nondestructive depth profiling by spectroscopic ellipsometry," *Appl. Phys. Lett.*, vol. 47, No. 4, Aug. 15, 1985, pp. 339–341.

M. Erman et al., "Analysis of ion–implanted GaAs by Spectroscopic ellipsometry," *Surface Science*, vol. 135, 1983, pp. 353–373.

J.B. Theeten et al., "Depth profiling and interface analysis using spectroscopic ellipsometry," *J. Vac. Sci. Technol.*, vol. 20, No. 3, Mar. 1982, pp. 471–475.

J.T. Lue et al., "The wavelength modulation spectrum of ion–implanted silicon," *J. Appl. Phys.*, vol. 53, No. 8, Aug. 1982, pp. 5617–5620.

D.E. Aspnes et al., "Direct Determination of Sizes of Excitations from Optical Measurements on Ion–Implanted GaAs," *Physical Review Letters*, vol. 48, No. 26, Jun. 28, 1982, pp. 1863–1866.

Q. Kim & Y.S. Park, "Ellipsometric investigation of ion–implanted GaAs," *Surface Science*, vol. 96, 1980, pp. 307–318.

Q. Kim et al., "Characterization of ion–implanted GaAs by ellipsometry," *J. Appl. Phys.*, vol. 51, No. 4, Apr. 1980, pp. 2024–2029.

D.E. Aspnes et al., "An investigation of ion–bombarded and annealed (111) surfaces of Ge by spectroscopic ellipsometry," *Surface Science*, vol. 96, 1980, pp. 294–306.

V.M. Gusev et al., "Interference method for measuring the effective thickness of ion–implated layers," *Soviet Physics—Semiconductors*, vol. 5, No. 5, Nov. 1971, pp. 737–739.

V.V. Galkin et al., "Implantation of 10–80 keV lithium ions in diamond," *Soviet Physics—Semiconductors*, vol. 4, No. 5, Nov. 1970, pp. 709–716.

V.V. Galkin et al., Ion–bombardment induced damage in diamond layers, *Soviet Physics—Solid State*, vol. 10, No. 3, Sep. 1968, pp. 706–708.

J.M. Leng et al., "Simultaneous measurement of six layers in a silicon on insulator film stack using spectrophotometry and beam profile reflectometry," *J. Appl. Phys.*, vol. 81, No. 8, Apr. 15, 1997, pp. 3570–3578.

U Zammit et al., "Optical absorption in ion implanted Si films," *Nuclear Instruments and Methods in Physics Research B*, vol. 96, 1995, pp. 241–244.

A. Rosencwaig et al., "Thermal wave characterization of semiconductors and superconductors," *Review of Progress in Quantitative Nondescriptive Evaluation*, vol. 8B, 1989, pp. 1195–1201.

J. Opsal, "Modulated interference effects and thermal wave monitoring of high–dose ion implantation in semiconductors," *Review of Progress in Quantitative Nondestructive Evaluation*, vol. 8B, 1989, pp. 1241–1245.

J. Bailey et al., "Subsurface defects in silicon investigated by modulated optical reflectance measurements," *Review of Progress in Quantitative Nondestructive Evaluation*, vol. 8B, 1989, pp. 1263–1271.

S. Lynch et al., "Non–destructive depth profiling of silicon ion implantation induced damage in silicon (100) substrates," *Thin Solid Films*, vol. 233, 1993, pp. 199–202.

I. Kasko et al., "Characterization of thin $TiSi_2$ films by spectroscopic ellipsometry and thermal wave analysis," *Microelectronic Engineering*, vol. 37, No. 38, 1997, pp. 455–460.

The damage layer thickness across the full dose range as determined by the spectroscopic ellipsometer.

The thermal wave response across the full dose range for P+ implant at 100 keV energy. The inset shows a close-up to the low sensitivity region.

COMBINATION THERMAL WAVE AND OPTICAL SPECTROSCOPY MEASUREMENT SYSTEMS

This is a continuation of U.S. patent application Ser. No. 09/499,974, filed Feb. 8, 2000 now U.S. Pat. No. 6,535,285.

TECHNICAL FIELD

The subject invention relates to a method and apparatus particularly suited for the analysis ion implantation at higher doses on semiconductor samples.

BACKGROUND OF THE INVENTION

There is a great need in the semiconductor industry for metrology equipment which can provide high resolution, nondestructive evaluation of product wafers as they pass through various fabrication stages. In recent years, a number of products have been developed for the nondestructive evaluation of semiconductor samples. One such product has been successfully marketed by the assignee herein under the trademark Therma-Probe. This device incorporates technology described in the following U.S. Pat. Nos. 4,634,290; 4,636,088, 4,854,710 and 5,074,669. The latter patents are incorporated herein by reference.

The Therma-Probe device monitors ion implant dose using thermal wave technology. In this device, an intensity modulated pump laser beam is focused on the sample surface for periodically exciting the sample. In the case of a semiconductor, thermal and plasma waves are generated in the sample which spread out from the pump beam spot. These waves reflect and scatter off various features and interact with various regions within the sample in a way which alters the flow of heat and/or plasma from the pump beam spot.

The presence of the thermal and plasma waves has a direct effect on the reflectivity at the surface of the sample. Features and regions below the sample surface which alter the passage of the thermal and plasma waves will therefore alter the optical reflective patterns at the surface of the sample. By monitoring the changes in reflectivity of the sample at the surface, information about characteristics below the surface can be investigated.

In the basic device, a second laser is provided for generating a probe beam of radiation. This probe beam is focused colinearly with the pump beam and reflects off the sample. A photodetector is provided for monitoring the power of reflected probe beam. The photodetector generates an output signal which is proportional to the reflected power of the probe beam and is therefore indicative of the varying optical reflectivity of the sample surface.

The output signal from the photodetector is filtered to isolate the changes which are synchronous with the pump beam modulation frequency. In the preferred embodiment, a lock-in detector is used to monitor the magnitude and phase of the periodic reflectivity signal. This output signal is conventionally referred to as the modulated optical reflectivity (MOR) of the sample.

Thermal wave technology is well suited for measuring lattice damage in crystalline materials and, therefore, serves as an excellent technology for monitoring the ion implant process in semiconductor materials. It is also known that optical methods, such as spectroscopic reflectance and spectroscopic ellipsometry, are sensitive to lattice damage through the effects of such damage on the optical properties of the material being implanted.

Typically, thermal waves are more sensitive in the region of low implantation, i.e. less than $10^{12}$ ions/cm$^2$ (arsenic at 30 KEV) than the optical methods. In the range of $10^{12}$ through $10^{14}$ ions/cm$^2$, it appears that optical and thermal waves are comparable in their ability to detect changes in lattice damage. At higher doses (of the same implant), amorphization sets in and the thermal wave signal is no longer monotonic with increasing dose and cannot be used reliably to monitor the implant process. In this high dose region, the optical methods are very sensitive and can unambiguously measure the thickness of the amorphous layer.

There is, however, damage above and below the amorphous layer which can still make an accurate measurement of total damage in the implanted material difficult using only optical methods. More specifically, the implantation process at high doses will create a large damaged region with a relatively smaller layer of amorphous material in the center thereof. This occurs because during the implantation process, the ions travel very quickly as they first strike the lattice. The fast passage through the lattice can result in little or no damage immediately beneath the surface. As the ions begin to slow down, the damage increases until at a certain depth, the damage is sufficient to produce amorphization. Amorphization represents the peak damage to the lattice. Ions which travel beyond the amorphous layer will cause further damage, but below the threshold for amorphization. Semiconductor manufacturers are interested in knowing both the thickness of the amorphous region, as well as the total extent of damage to the lattice which would include the damaged regions both above and below the amorphous layer.

Thermal waves are intrinsically more sensitive to total damage than the optical methods. Therefore, by combining thermal waves with spectroscopic measurements, one can provide a means for sensitive and unambiguous monitoring of the ion implant process throughout the entire range. More specifically, one can use the data derived from the thermal wave measurements to provide an indication of the full extent of the damaged region. Data obtained from a spectroscopic measurements can be used to provide an indication of the thickness of the amorphous layer. By combining these two sets of measurements, one can provide an accurate profile of the damage as a function of depth below the surface of the semiconductor wafer.

The concept of combining thermal wave measurements with other optical measurements is disclosed in prior U.S. Pat. No. 5,978,074, issued Nov. 2, 1999, and is assigned to the same assignee as the subject invention and is incorporated herein by reference. This patent describes the need to obtain additional measurements where the sample is more complex. In one aspect of that patent disclosure, a conventional thermal wave detection system was modified to increase the amount of data which could be obtained. For example, a steering system was provided for varying the distance between the pump and probe beam spots as measurements were taken. Another approach was to obtain a sequence of measurements at various pump beam modulation frequencies.

The prior patent also discussed the advantages of combining spectroscopic reflectivity measurements with the thermal wave measurements. Various additional measurements were suggested including the assignee's proprietary beam profile reflectometry and beam profile ellipsometry techniques. The latter two approaches are described in U.S. Pat. Nos. 4,999,014 and 5,181,080, both of which are incorporated herein by reference.

The principal application for the tool described in U.S. Pat. No. 5,87,974 relates to measuring thin metal films formed on semiconductor samples. The latter patent did not disclose the advantages of combining thermal wave measurements with spectroscopic ellipsometry measurements. Further, the latter patent did not discuss the specific concept of using a thermal wave measurement to provide information on the full extent of a damage layer, while using another optical measurement to provide an indication of the amorphous layer.

Accordingly, it is an object of the subject invention to provide a new method and apparatus which provides additional measurement capabilities.

It is another object of the subject invention to provide a method and apparatus particularly suited to evaluating high dopant concentrations in semiconductors.

It is a further object of the subject invention to provide a method and apparatus which combines measurements of modulated optical reflectivity with modulated spectroscopic ellipsometry.

SUMMARY OF THE INVENTION

In accordance with these and other objects, the subject invention includes a method wherein a sample is characterized through a combination of measurements which include both a thermal or plasma wave measurement and a spectroscopic measurement. The thermal/plasma wave measurement is obtained by periodically exciting a region on the sample with an intensity modulated pump beam. A probe beam is directed to a region on the sample surface which has been periodically excited. Changes in power of the reflected probe beam are monitored to obtain the modulated optical reflectometry of the sample.

In accordance with the subject method, a separate spectroscopic measurement is also obtained. To obtain this measurement, a polychromatic light source generates a polychromatic probe beam which is directed to reflect off the sample. The intensity of the reflected polychromatic probe beam can be measured to obtain spectroscopic reflectance data. Alternatively, or in addition, the change in polarization state of the polychromatic probe beam can be measured to obtain ellipsometric information. Additional measurement technologies can also be employed.

In accordance with the subject invention, data corresponding to the modulated optical reflectivity signal is combined with the spectroscopic data to more accurately characterize the sample. In one preferred embodiment, the system is used to more fully characterize high dosage levels of ion implantation in a semiconductor wafer. In this approach, the modulated optical reflectivity signal is useful for characterizing the full extent of the damaged region, while the spectroscopic ellipsometric information is used to characterize the extent of the amorphous layer.

DETAILED DESCRIPTION OF THE PREFERRED EMBODIMENT

Figure 1:
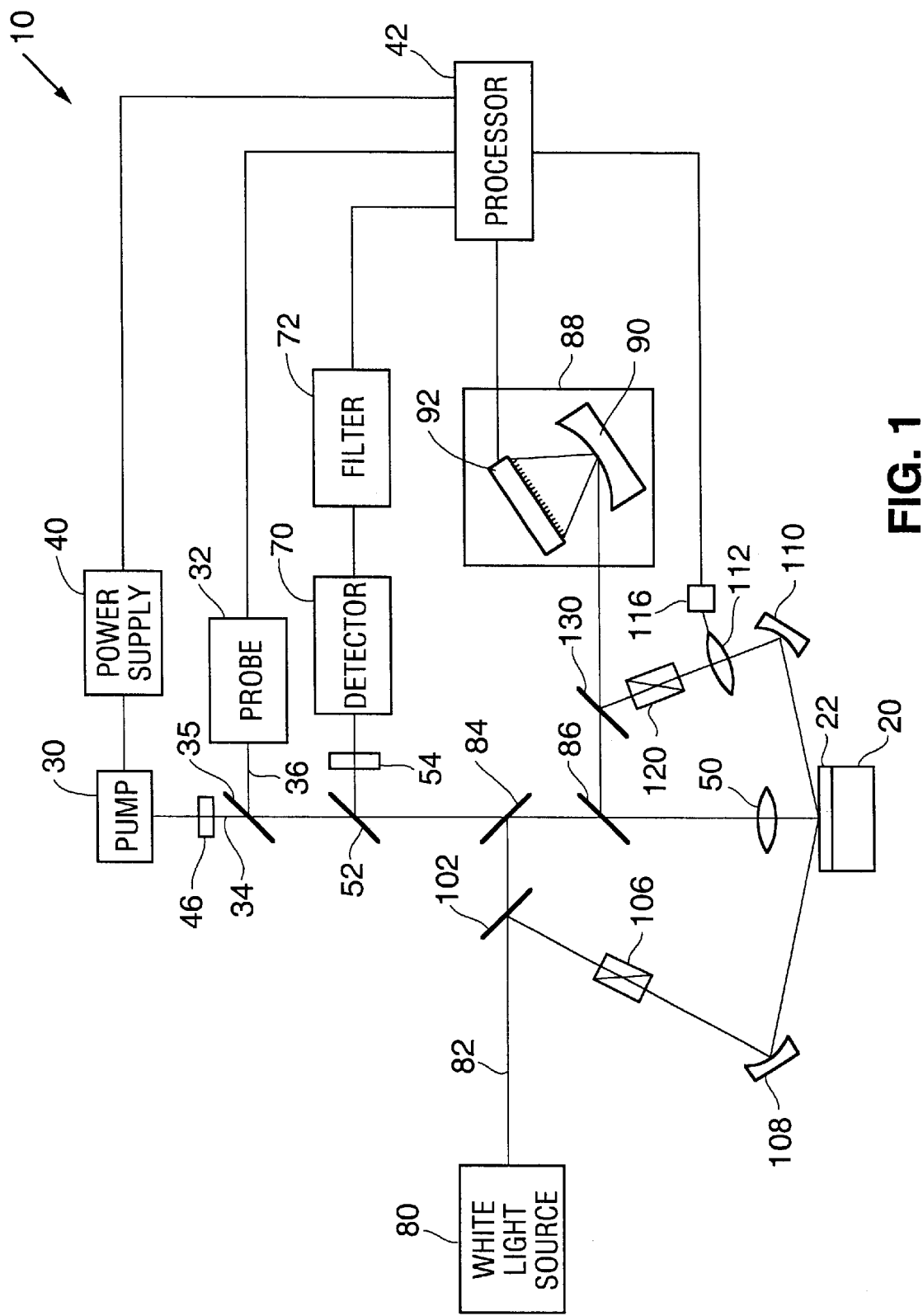
FIG. 1 is a schematic diagram of the apparatus for carrying out the methods of the subject invention.

FIG. 1 is a simplified diagram of the basic components of an apparatus 10 which can be used to take the measurements useful in applying the methods of the subject invention. The apparatus is particularly suited for measuring characteristics of semiconductor wafers 20. In one important aspect of the invention, the device is used to characterize levels of ion implantation in the wafer. The device could also be used to characterize properties of one or more thin film layers 22 on top of the wafer.

In accordance with the subject invention, the apparatus includes a first measurement system for generating thermal and/or plasma wavers and monitoring the propagation of these waves in the sample. This portion of the system includes a pump laser 30 for exciting the sample and a probe laser 32 for monitoring the sample. Gas, solid state or semiconductor lasers can be used. As described in the assignee's earlier patents, other means for exciting the sample can include different sources of electromagnetic radiation or particle beams such as from an electron gun.

In the preferred embodiment, semiconductor lasers are selected for both the pump and probe lasers due to their reliability and long life. In the illustrated embodiment, pump laser 30 generates a near infrared output beam 34 at 790 nm while probe laser 32 generates a visible output beam 36 at 670 nm. Suitable semiconductor lasers for this application include the Mitsubishi ML6414R (operated at 30 mW output) for the pump laser and a Toshiba Model 9211 (5 mW output) for the probe laser. The outputs of the two lasers are linearly polarized. The beams are combined with a dichroic mirror 38. It is also possible to use two lasers with similar wavelengths and rely on polarization discrimination for beam combining and splitting.

Pump laser 30 is connected to a power supply 40 which is under the control of a processor 42. The output beam of laser 30 is intensity modulated through the output of power supply 40. The modulation frequency has a range running from 100 KHz to 100 MHz. In the preferred embodiment, the modulation frequency can be set up to 125 MHz. As described in the above cited patents, if an ion laser is used to generate the pump beam, the intensity modulation can be achieved by a separate acousto-optic modulator.

Prior to reaching the beam combining mirror 36, the probe beam 34 passes through a tracker 46. Tracker 46 is used to control the lateral position of beam 34 with respect to the probe beam. In some measurements, the two beams will be positioned so that the spots will overlap on the sample surface. In addition, measurements can be taken at various spacings between the pump and probe beam spots. Measurements at different spatial separations are discussed in greater detail in U.S. Pat. No. 5,978,074.

The beams are directed down to the sample 20 through a microscope objective 50. Objective 50 has a high n.a., on the order of 0.9, and is capable of focusing the beam to a spot size on the order of a few microns and preferably close to one micron in diameter. The spacing between the objective and the sample is controlled by an autofocus system not shown herein but described in U.S. Pat. No. 5,978,074.

The returning reflected beams 34 and 36 are reflected by beam splitter 52. A filter 54 is provided to remove the pump beam light 34 allowing the probe beam light to fall on the photodetector 60. Detector 60 provides an output signal which is proportional to the power of the reflected probe beam 36. Detector 60 is arranged to be underfilled so that its output can be insensitive to any changes in beam diameter or position. In the preferred embodiment, detector 60 is a quad cell generating four separate outputs. When used to measure reflected beam power, the output of all four quadrants are summed. As described in U.S. Pat. No. 5,978,074, the apparatus can also be operated to measure beam deflection. In the latter case, the output of one adjacent pair of quadrants is summed and subtracted from the sum of the remaining pair of quadrants.

The output of the photodetector 60 is passed through a low pass filter 72 before reaching processor 42. One function of filter 72 is to pass a signal to the processor 42 proportional to the DC power of the reflected probe. A portion of filter 72 also functions to isolate the changes in power of the reflected probe beam which are synchronous with the pump beam modulation frequency. In the preferred embodiment, the filter 72 includes a lock-in detector for monitoring the magnitude and phase of the periodic reflectivity signal. Because the modulation frequency of pump laser can be so high, it is preferable to provide an initial down-mixing stage for reducing the frequency of detection. Further details of the preferred filter and alternatives are described in U.S. Pat. No. 5,978,074. For example, it would be possible to use a modulated pump beam to obtain an optically heterodyned signal as described in U.S. Pat. No. 5,206,710, incorporated herein by reference.

To insure proper repeatability of the measurements, the signals must be normalized in the processor. As noted above, the DC reflectivity of the probe beam is derived from detector 60. In addition, the DC output powers of the pump and probe lasers are monitored by incident power detectors (not shown) and provided to the processor. The signals are further normalized by taking a measurement of the power of the pump beam 34 after it has been reflected by another detector (not shown). This measurement is used to determine the amount of pump energy which has been absorbed in the sample. The DC signal for both the incident pump and probe beam powers as well as the reflected beam powers are used to correct for laser intensity fluctuations and absorption and reflection variations in the samples. In addition, the signals can be used to help calculate sample parameters.

In accordance with the subject invention, in addition to the thermal wave measurement system, a separate spectroscopic measurement system is also included. This additional system includes a polychromatic or white light source 80. The white light source can be defined by a single broadband lamp, such as a xenon arc lamp. Alternatively, the white light source could be defined by two or more lamps such as a xenon arc lamp to cover of the visible light ranges and a separate deuterium lamp to cover the ultraviolet ranges.

The output from the white light source 80 is a polychromatic probe the beam 82. The beam can be redirected by a splitter 84 towards the sample. The beam 82 is focused onto the sample by microscope objective 50. The reflected beam is redirected by splitter 86 to a spectrometer 88. The spectrometer can be of any type commonly known and used in the prior art. In the illustrated embodiment, the spectrometer includes a curved grating 90 which functions to angularly spread the beam as a function of wavelengths. A photodetector 92 is provided for measuring the beam. Photodetector 92 is typically a photodiode array with different wavelengths or colors falling on each element in the array. Other alternative detectors would include a CCD camera or photomultiplier. It should be noted that it is within the scope of this invention to use a monochrometer and obtain measurements serially (one wavelength at a time) using a single detector element.

The output of detector 92 is supplied to the processor 42. When the polychromatic light beam 82 follows the path discussed above, the output of detector 92 would correspond to the reflectance of the sample. In accordance with the subject invention, polychromatic light beam 82 can also be used to obtain spectroscopic ellipsometric measurements.

In order to obtain spectroscopic ellipsometric measurements, a beam splitter 102 can be placed in the path of the polychromatic light beam 82. Beams splitter 102 redirects the beam through polarizer 106 to create a known polarization state. Polarizer 106 can be a linear polarizer made from a quartz Rochon prism. The polarized probe beam is focused onto the sample 20 by a curved mirror 108. The beam strikes the sample at an angle on the order of 70 degrees to the normal to maximize sensitivity. Based upon well-known ellipsometric principles, the reflected beam will generally have a mixed linear and circular polarization state after interacting with the sample, as compared to the linear polarization state of the incoming beam. The reflected beam is redirected by mirror 110 through a rotating compensator 112. Compensator 112 introduces a relative phase delay or phase retardation between a pair of mutually orthogonal polarized optical beam components. The amount of phase retardation is a function of the wavelength, the dispersion characteristics of the material used to form the compensator and the thickness of the compensator. The compensator is rotated by motor 116 at an angular velocity ω about an axis substantially parallel to the propagation direction of the beam. In the preferred embodiments, compensator 112 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation over the wavelength range of interest.

After passing through the compensator 112, the beam interacts with the analyzer 120. Analyzer 120 service to mix a polarization states of the beam. In this embodiment, analyzer 120 is another linear polarizer. The rotating compensator spectroscopic ellipsometer illustrated herein is described in greater detail in U.S. Pat. No. 5,973,787 assigned to the same assignee and incorporated herein by reference. While a rotating compensator ellipsometer is disclosed, the scope of the subject invention is intended to include any of the other conventional spectroscopic ellipsometer configurations. These would include rotating analyzer systems as well as fixed element systems that rely on photoelastic modulators for retardation.

After the beam passes analyzer 120 it is reflected by beam splitter 130 and directed to the spectrometer 88. As noted above, grating 90 disperses the beam onto the array detector 92. The measured output from the spectrometer corresponds to the change in polarization state of the beam and from this information, the traditional ellipsometric parameters Ψ and Δ can be derived.

The optical layout in FIG. 1 is intended to illustrate how both a thermal wave detection system and a spectroscopic detection system, and in particular, a spectroscopic ellipsometric system might be employed to obtain measurements at generally the same spot on the surface of the sample and in a near contemporaneous fashion. In this manner, the combination of the measurements results will produce a more accurate result.

The combination of the two metrology devices in a single tool in addition to providing more accurate results provides economic benefits as well. For example, a single tool has a smaller footprint and therefore takes up less space in the semiconductor fab. By combining technologies in a single tool, costs can be reduced by eliminating duplicate subsystems such as wafer handlers and computers. Finally, the combination can simplify and streamline decision making since the information from the two measurement modalities can be coordinated instead of producing conflicting results which can occur if two separate devices were used.

It is believed that a combination thermal wave and spectroscopic inspection device will be particularly useful for analyzing ion implantation in semiconductor samples. To determine the efficacy of this approach, experiments were run to obtain data on similarly prepared wafers on the assignee's Therma-Probe thermal wave device (Model TP-500), as well as two of assignee's Opti-Probe models, the 3260 for the broadband spectroscopic measurements and the 5240 to obtain broadband spectroscopic ellipsometric measurements.

In these experiments, a total of 23 wafers each having a diameter of 150 mm were prepared on a GSD-600 ion implanter using $P^+$ ions at 100 keV energy or $As^+$ ions at 30 keV. Each wafer had a uniform dose with 20 wafers having the $P^+$ dose within the range from 1e10 to 1e16 ions/cm$^2$ and three wafers having the $As^+$ ion dose of 5.4e12±5% ions/cm$^2$. The wafers were not treated for thermal annealing of the crystalline damage. 21-point map broadband (210–780 nm) spectroscopic ellipsometry (SE) measurements were performed on the Opti-Probe 5240 and thermal wave measurements were done on the Therma-Probe 500 (TP-500) ion implant monitoring tool. For added comparison, broad band (190–780 nm) spectral reflectance (SR) was done on an Opti-Probe 3260 (OP-3260).

As a part of this investigation, measurement recipes were developed for the OP-5240 and OP-3260 while the ion implant monitoring recipes were readily available on the TP-500. For ion implant monitoring purposes, a simple model was applied with a single damage layer on undoped crystalline silicon and with an overlayer of thermal oxide. The wafers under study had a nominal 100 Å of thermal oxide deposited prior to ion implantation. The optical properties of thermal oxide are well known and the standard library lookup table values were used for the oxide dispersion while the thickness of the top oxide layer was allowed to vary as a fitting parameter. A critical point model with five harmonic oscillators was used for the optical dispersion of the damage layer. Initial recipe development involved fitting of the experimental data with variable dispersion for the damage layer as well as the damage layer and the oxide thicknesses.

Figure 2:
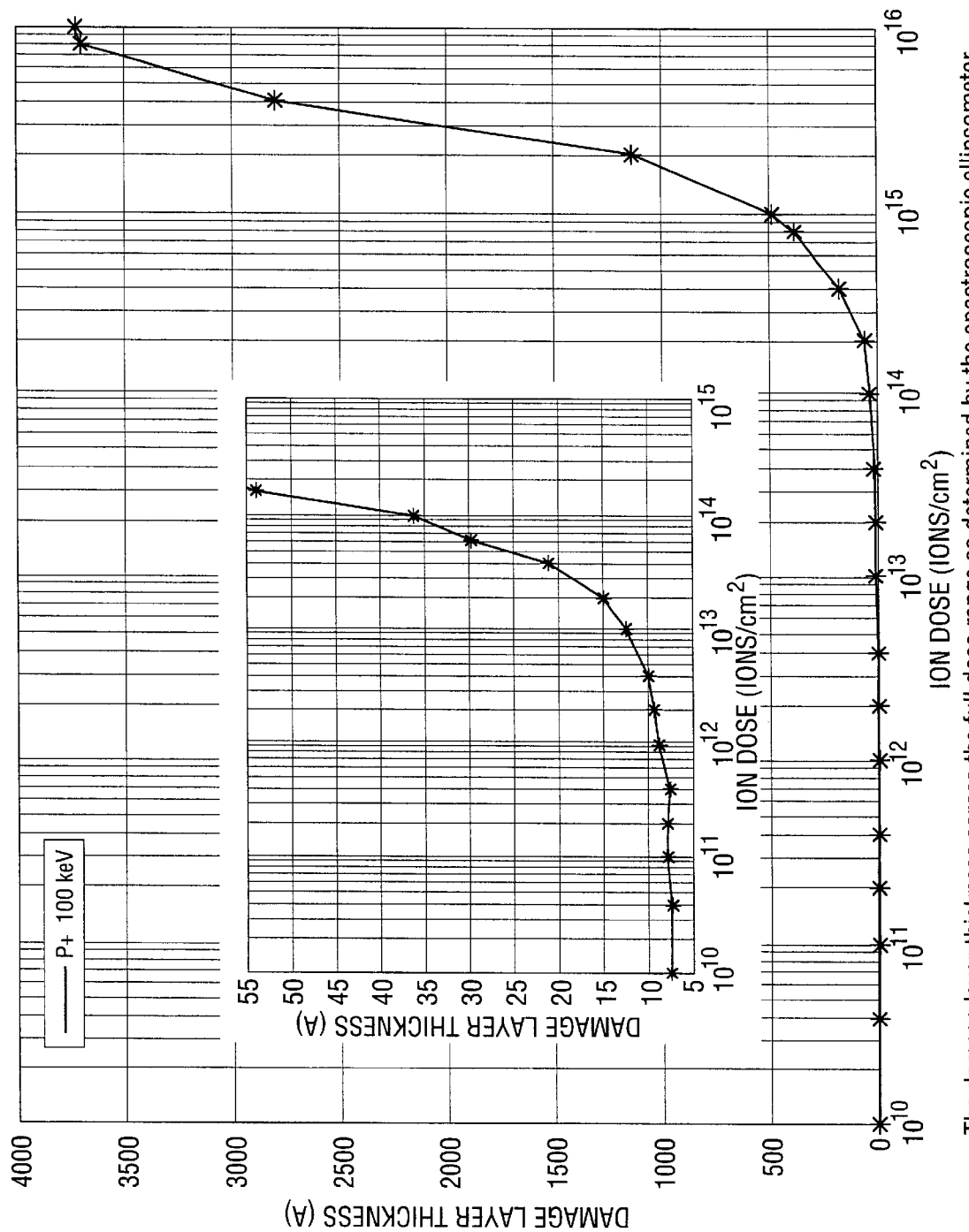
FIG. 2 is a graph illustrating the damage layer thickness across a full ion implant dose range as measured by a spectroscopic ellipsometer.
Figure 3:
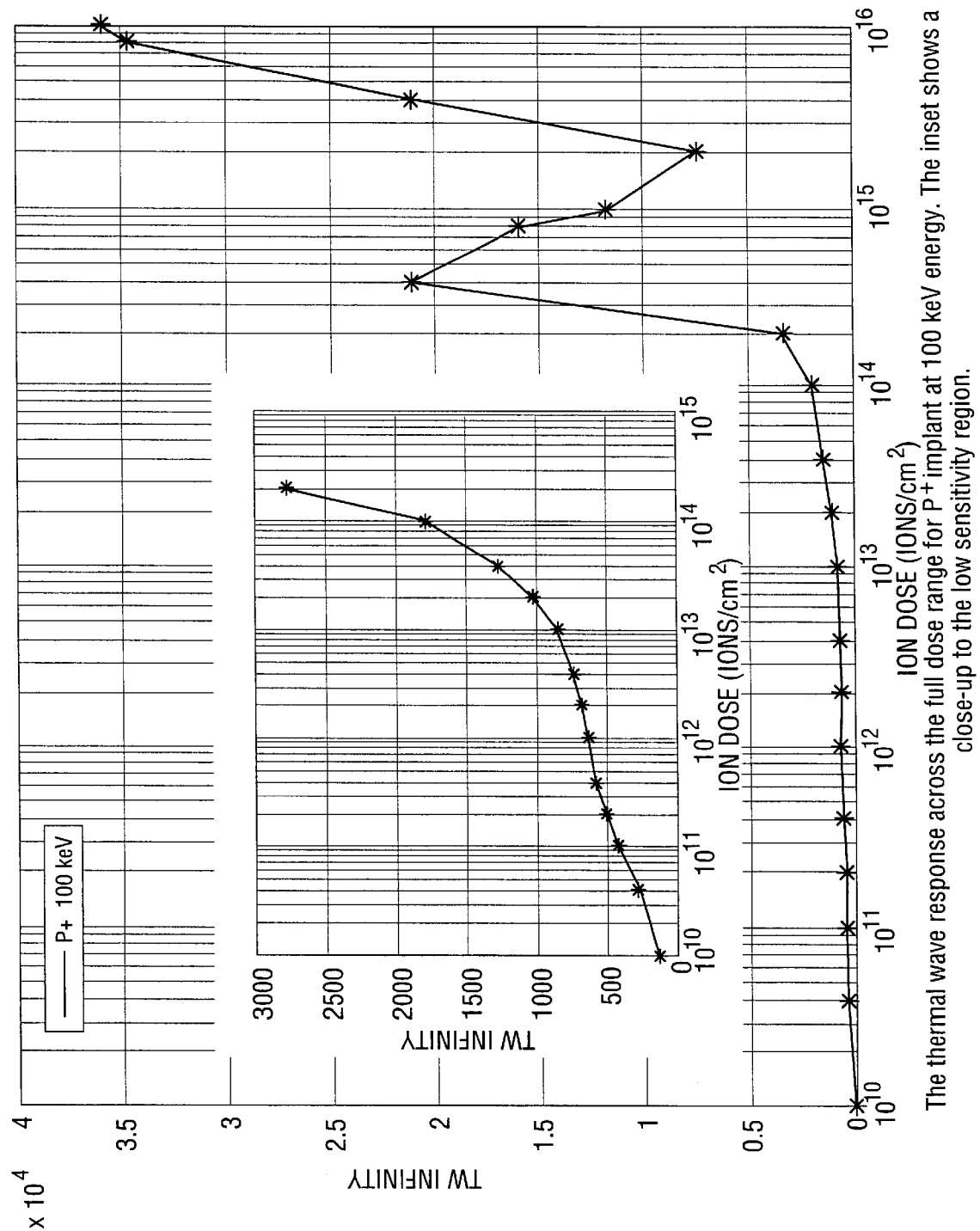
FIG. 3 is a graph illustrating the thermal wave response across a full ion implant dose range.

The phase transition from crystalline-like to amorphous-like silicon was observed between doses 2e14 and 4e14 ions/cm$^2$ for the Phosphorous implant at 100 keV. The dose range can then be divided into a low dose region (1e 10–1e14), a medium dose region (1e14–6e14) and a high dose region (6e14–1e16). A separate recipe is needed for the curve fitting of each dose region due to the limited dynamic range of the fitting algorithm. FIG. 2 shows the results of curve fitting for the full range of ion doses characterized with spectroscopic ellipsometry. FIG. 3 has the results for the thermal wave technique. The characteristic low sensitivity plateau region around the 700 TW unit is missing in the SE results. Furthermore, the negative slope at higher doses, which is related to the optical interference effects in the amorphous layer, is not an issue for the SE measurements.

In addition to the dose sensitivity, the instrumental noise needs to be included in any analysis of implant monitoring capability. The dose sensitivity S in units of %-change in a monitoring parameter per %-change in ion dose can be estimated from $$S = \frac{(P_2 - P_1)/(P_2 + P_1)}{(D_2 - D_1)/(D_2 + D_1)}$$

where P refers to the monitoring parameter, D is the ion dose, and the subscript 1 and 2 refer to the samples in question.

To estimate the noise for each technology, the short term repeatability of map measurements was determined within a one to two hour period with 10 cycles of wafer loading, and the long term repeatability was estimated from map measurements repeated once a day for five consecutive days. The repeatability is defined as the standard deviation at 1-σ and the percent notation %σ=1-σ/mean mean is used here. For each technology, the detection limit DL in %-change in dose can then be estimated from $$DL = \frac{\%\sigma}{S}$$

Figure 4:
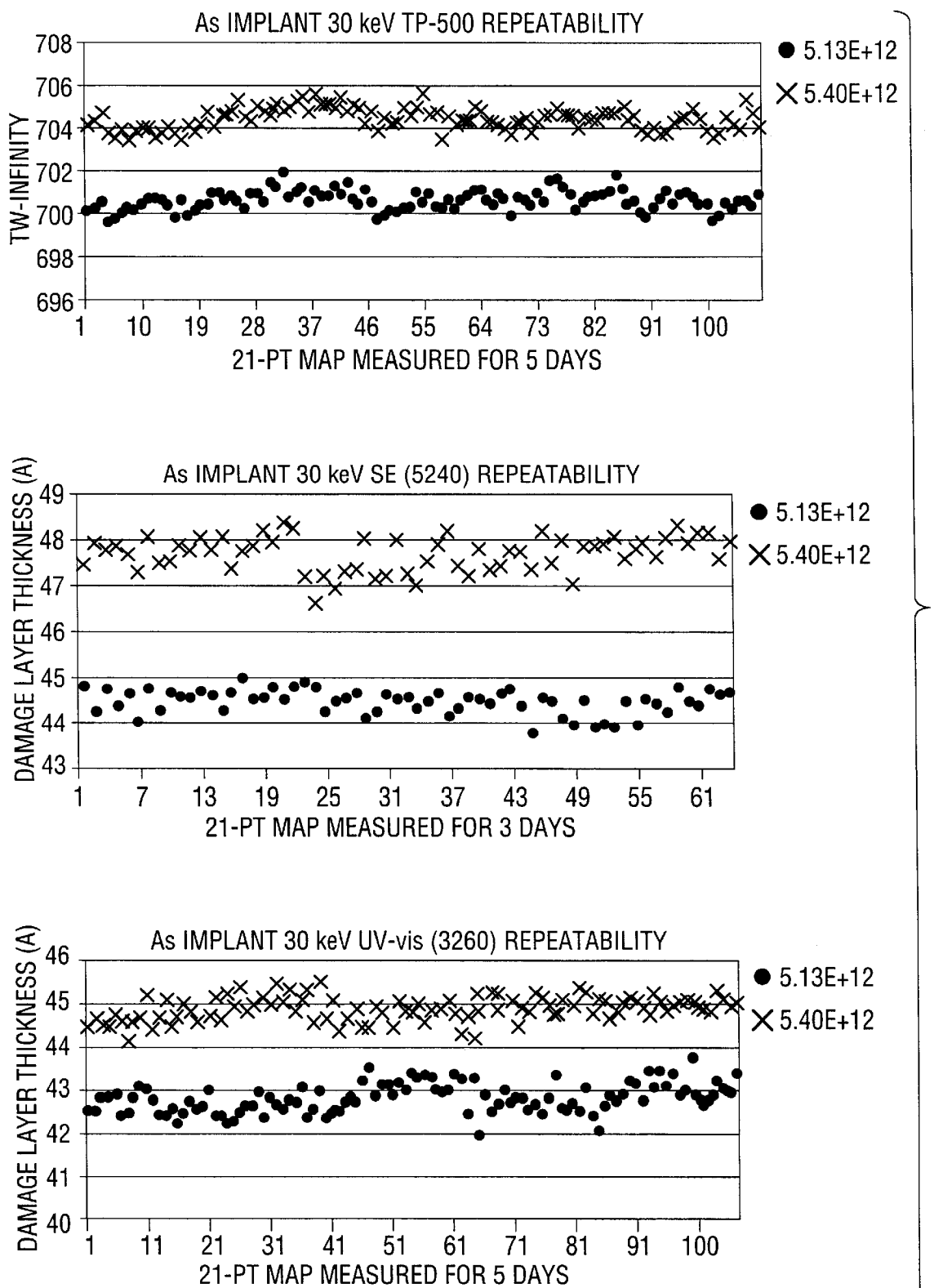
FIG. 4 is a statistical process control plot of long term monitoring of a silicon wafers implanted with arsenic using the three different measurement technologies.
Figure 5:
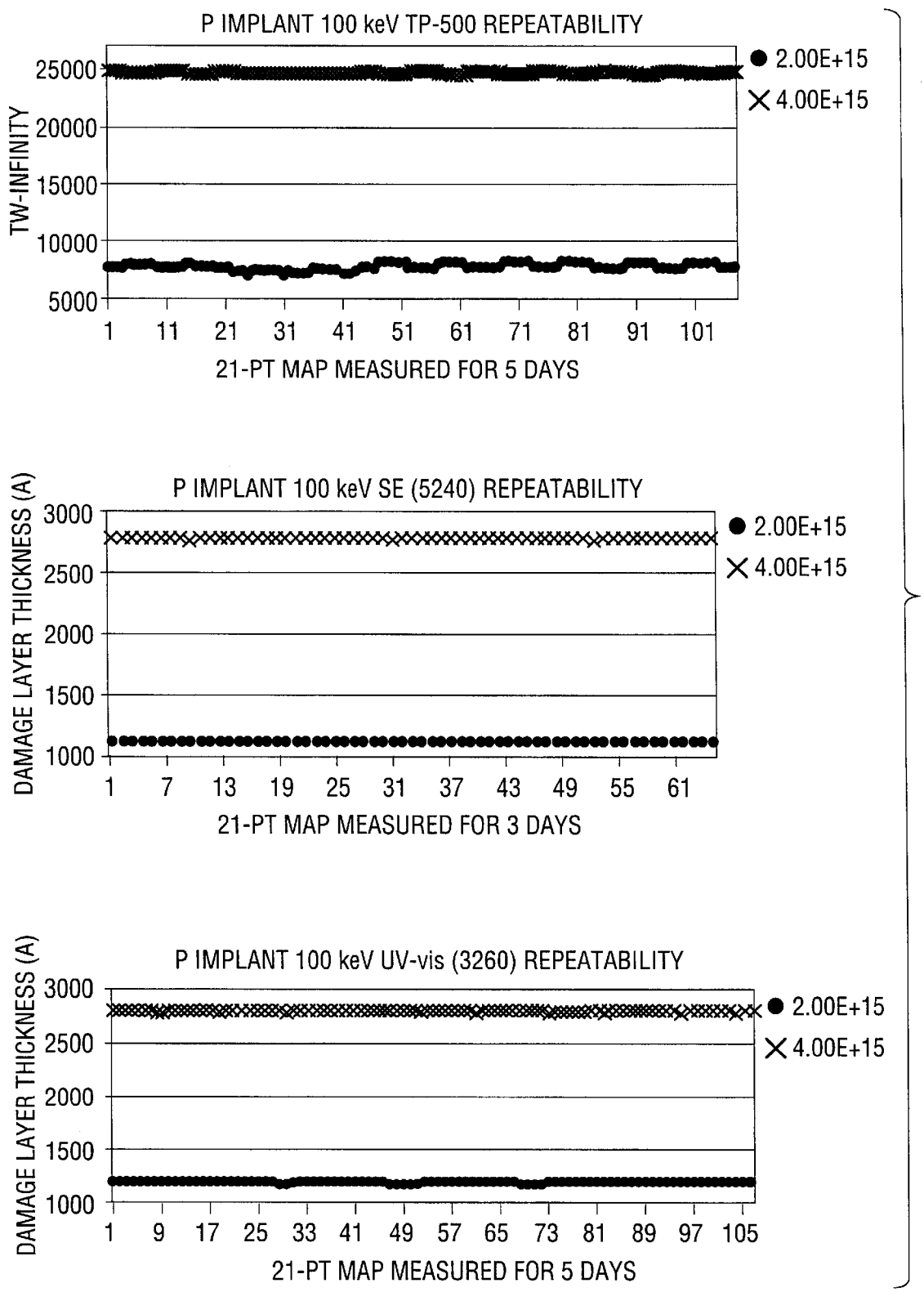
FIG. 5 is a statistical process control plot of long term monitoring of a silicon wafers implanted with arsenic using the three different measurement technologies.

The monitoring results for four sample wafers are illustrated in FIG. 4 with the statistical process control (SPC) plots. The data in Tables 1 and 2 are analyzed to extract the low dose and high dose detection limits in %-dose for each technology. The spectroscopic ellipsometry technology shows superior performance in the high dose detection with a factor of 30 improvement in comparison to the industry standard thermal wave technology. For low dose detection the SE performance is comparable to TP-500.

Table 1 below illustrates the long term detection at high dose with each technology. The monitoring parameter for TP-500 is the thermal wave signal in TW units and for the OP-tools the monitoring parameter is the damage layer thickness in Å.

| HIGH DOSE | | TP-500 | OP-5240* | OP-3260 |
| --- | --- | --- | --- | --- |
| P 100 keV | Average | 7825.93 | 1120.36 | 1173.265 |
| 2.00E+15 | 1-σ | 205.066 | 0.271 | 0.802 |
| | % 1-σ | 2.620 | 0.024 | 0.068 |
| P 100 keV | Average | 24667.05 | 2793.66 | 2795.649 |
| 4.00E+15 | 1-σ | 62.734 | 0.568 | 0.589 |
| | % 1-σ | 0.254 | 0.020 | 0.021 |
| Sensitivity (%-per-%) | | 1.555 | 1.283 | 1.226 |
| Detection limit (% dose) | | 1.685 | 0.019 | 0.056 |

*3 days of data was acquired

Table 2 below shows the long term detection at low dose with each technology. The monitoring parameter for TP-500 is the thermal wave signal in TW units and for the OP-tools the monitoring parameter is the damage layer thickness in Å.

| LOW DOSE | | TP-500 | OP-5240* | OP-3260 |
| --- | --- | --- | --- | --- |
| As 30 keV | Average | 700.61 | 44.45 | 42.825 |
| 5.13E+12 | 1-σ | 0.265 | 0.130 | 0.261 |
| | % 1-σ | 0.038 | 0.293 | 0.610 |
| As 30 keV | Average | 704.42 | 47.71 | 44.887 |

-continued

| LOW DOSE | | TP-500 | OP-5240* | OP-3260 |
|---|---|---|---|---|
| 5.40E+12 | 1-$\sigma$ | 0.382 | 0.235 | 0.175 |
| | % 1-$\sigma$ | 0.054 | 0.494 | 0.390 |
| Sensitivity (%-per-%) | | 0.106 | 1.379 | 0.917 |
| Detection limit (% dose) | | 0.512 | 0.358 | 0.666 |

*3 days of data was acquired

As can be seen from the above data, both the thermal wave measurements and the spectroscopic measurements can provide useful information about ion implantation in semiconductor wafers. In accordance with the subject invention, this data can be combined in order to improve the analysis of the sample and reduced ambiguities.

There are a number of approaches which are available to combine data from different technologies. One could use the data independently to arrive at separate approximations of the ion implantation dose of the sample and then derive a final result by taking a weighted average of the independent solutions. Preferably, a more robust analysis will be performed that combines data from both measurements in iterative process to reach a best fit solution. Such iterative approaches for combining data from multiple measurements are now more well known in the metrology field. For example see "Simultaneous Measurement of Six Layers in a Silicon on Insulator Film Stack Using Spectrophotometry and Beam Profile Reflectometry," Leng, et. al, Journal of Applied Physics, Vol 81, No. 8, Apr. 15, 1997.

The subject invention is not limited to the particular algorithm used to derive the characteristics of the individual layers. In addition to the more conventional least square fitting routines, alternative approaches can be used. For example, the high level of computing power now available permits approaches to be utilized which include genetic algorithms. One example of the use of genetic algorithms to determine the thickness of thin film layers can be found in "Using Genetic Algorithms with Local Search for Thin Film Metrology," Land, et. al., Proceeding of the Seventh International Conference on Genetic Algorithms, July 19–23, page 537, 1997. See also, U.S. Pat. No. 5,864,633, incorporated herein by reference.

In one particular implementation of the subject invention, the thermal wave signals and the spectroscopic ellipsometer signals are combined to analyze the extent of damage induced by ion implantation. As noted above, the spectroscopic ellipsometer signals are particularly useful in characterizing the extent of the amorphous layer created by the ion implantation process. Conversely, the thermal wave data is particularly sensitive to the overall damage layer. By properly combining the data with suitable algorithms, a full characterization of the ion implant damage as a function of depth can be achieved. Alternatively, the spectroscopic reflectivity measurements could be combined with the thermal wave measurements to perform this analysis.

In addition to analyzing ion implantation processes, the combination of thermal wave and spectroscopic ellipsometric measurements can be used to reduce ambiguities in measurements associated with other aspects of semiconductor fabrication. For example, this combination could be used to analyze characteristics of various thin films of the sample. Such thin films can include oxides, nitrides and metals. Information obtained from the two or more independent measurements allows one to more accurately determined the characteristics of those layers. Those characteristics could include, for example, thickness, index of refraction, extinction coefficient, density and thermal conductivity.

Is also within the scope of the subject invention to combine additional technologies to the measurement beyond those illustrated in FIG. 1. For example, measurement technologies such as the assignee's proprietary beam profile reflectometry and beam profile ellipsometry could be used. The addition of such further measurement modules is described in assignee's prior U.S. Pat. No. 5,978,074.

While the subject invention has been described with reference to a preferred embodiment, various changes and modifications could be made therein, by one skilled in the art, without varying from the scope and spirit of the subject invention as defined by the appended claims.

We claim:

1. A method of evaluating characteristics of a semiconductor wafer wherein the upper region thereof has been implanted with dopants, said method comprising the steps of:
    periodically exciting a region on the surface of the wafer;
    monitoring the modulated optical reflectivity induced by said periodic excitation and generating first output signals in response thereto;
    obtaining spectroscopic ellipsometric information from the same region on the sample surface and generating second output signals in response thereto; and
    evaluating the implantation characteristics based on a combination of the first and second output signals.

2. A method as recited in claim 1, wherein said step of obtaining spectroscopic ellipsometric information comprises the further steps of:
    directing a polychromatic probe beam having a known polarization to reflect off the surface of the sample; and
    monitoring the change in polarization state of the probe beam induced by reflection at a plurality of wavelengths.

3. A method as recited in claim 1, wherein the first and second output signals are combined in an iterative process to find a best fit solution.

4. An apparatus for evaluating the characteristics of a semiconductor wafer wherein the upper region thereof has been implanted with dopants, said apparatus comprising:
    an intensity modulated pump laser beam, said pump laser beam being directed to a spot on the surface of the sample for periodically exciting the wafer;
    a probe laser beam being directed to a spot on the surface of the wafer within a region which has been periodically excited and is reflected therefrom;
    a detector for measuring the power of the reflected probe laser beam and generating a first output signal in response thereto;
    a broadband polychromatic light source for generating a polychromatic probe beam having a known polarization state, said polychromatic probe beam being directed to reflect off a spot on the surface of the sample;
    an analyzer for monitoring the change in polarization state of the reflected polychromatic probe beam and generating a plurality of second output signals corresponding to a plurality of different wavelengths within the polychromatic probe beam; and
    a processor for filtering the first output signal to provide a measure of the magnitude or phase of the modulated optical reflectivity of the sample, said processor further functioning to monitor the second output signals and with the first and second output signals being combined to evaluate the implantation characteristics of the wafer.

5. An apparatus as recited in claim 4, wherein the probe beam from the polychromatic light source is directed to the same location as the probe laser beam is directed.

6. An apparatus as recited in claim 4, further including a steering means for adjusting the lateral separation between the pump and probe laser beam spots on the surface of the sample and wherein a plurality of measurements are taken at different separations between the pump and probe laser beam spots.

7. An apparatus as recited in claim 4, further including a means for varying the modulation frequency of the pump laser beam and wherein a plurality of measurements are taken at different modulation frequencies.

8. An apparatus as recited in claim 4, wherein the first and second output signals are combined in an iterative process to find a best fit solution.

* * * * *